(12) United States Patent
Lois

(10) Patent No.: US 6,183,450 B1
(45) Date of Patent: Feb. 6, 2001

(54) CATHETER DE-CLOGGING DEVICE

(76) Inventor: William A Lois, 2233 E. 65th St., Brooklyn, NY (US) 11234

( * ) Notice: Under 35 U.S.C. 154(b), the term of this patent shall be extended for 0 days.

(21) Appl. No.: 09/325,805

(22) Filed: Jun. 4, 1999

(51) Int. Cl.[7] .................................................. A61M 25/00
(52) U.S. Cl. .................... 604/267; 604/164.01; 606/159
(58) Field of Search ................................... 604/267, 266, 604/264, 175, 523, 533, 539, 164.01, 164.12, 164.13, 165.01, 165.02; 606/159, 167, 171, 185; 600/434, 585

(56) References Cited

U.S. PATENT DOCUMENTS

| | | |
|---|---|---|
| 3,956,011 | 5/1976 | Carleton . |
| 4,459,318 | 7/1984 | Hyans . |
| 4,509,947 | 4/1985 | Lattin . |
| 4,696,667 | 9/1987 | Masch . |
| 4,698,058 | 10/1987 | Greenfeld et al. . |
| 5,030,213 | 7/1991 | Rumberger et al. . |
| 5,370,653 * | 12/1994 | Cragg .................................... 606/170 |
| 5,492,530 | 2/1996 | Fischell et al. . |
| 5,653,696 | 8/1997 | Shiber . |
| 5,782,848 * | 7/1998 | Lennox ................................ 606/159 |
| 5,882,329 * | 3/1999 | Patterson et al. ...................... 604/49 |
| 6,045,623 * | 4/2000 | Cannon ................................... 134/8 |

* cited by examiner

*Primary Examiner*—Glenn K. Dawson
*Assistant Examiner*—Jennifer Maynard
(74) *Attorney, Agent, or Firm*—Michael I. Kroll

(57) ABSTRACT

A catheter cleaning device for clearing a catheter of obstructions. The catheter cleaning device includes an elongate hollow housing including first and second slots extending along opposing sides thereof and first and second lateral slots extending perpendicular to a respective one of the first and second slots, a guide member encircling the housing and including a bar extending across a diameter thereof and through both the first and second slots, a guide wire extending from the bar and an adapter for connecting the device to the catheter. The adapter includes a recess extending therethrough for the guide wire to pass out of the housing and into the catheter. The first and second lateral slots allow for rotation of the guide member and thus turning of the guide wire. Turning of the guide wire causes the guide wire to scrape against the obstruction thereby breaking the obstruction into smaller pieces and clearing the catheter. The guide wire has a length substantially equal to a length of the catheter and an end of said guide wire is able to bow upon contacting the obstruction.

10 Claims, 7 Drawing Sheets

CATHETER DE-CLOGGING DEVICE

BACKGROUND OF THE INVENTION

1. Field of the Invention

The present invention relates generally to catheters and, more specifically, to a device able to be readily connected to an end of a catheter for breaking up and removing obstructions within a lumen of the catheter and a method for breaking up an obstruction within a catheter.

2. Description of the Prior Art

Numerous types of catheter clearing and cleaning devices have been provided in the prior art. For example, U.S. Pat. Nos. 3,956,011; 4,698,058, 4,459,318; 4,509,947; 4,696,667; 5,030,213; 5,492,530 and 5,653,696 all are illustrative of such prior art. While these catheter clearing and cleaning devices may be suitable for the purposes for which they were designed, they would not be as suitable for the purposes of the present invention, as hereinafter described.

U.S. Pat. No. 3,956,011

Inventor: John S. Carleton

Issued: May 11, 1976

Method for cleaning a suction catheter including providing a sterilized environment for the catheter prior to use and convenient vessel for cleaning the catheter between each use with a single patient. The method further includes the steps of cleaning the catheter before each use by securing the suction catheter depending from a holder into an opening in a vessel, the opening mating with the holder, after using the catheter in connection with treating a patient; flowing a cleaning solution into the vessel to the level of soil on the catheter suspended therein; and suctioning substantially all of the cleaning solution from the vessel through the catheter prior to disposing of both catheter and cleaning system after their use in connection with a single patient.

U.S. Pat. No. 4,459,318

Inventor: Thomas E. Hyans

Issued: Jul. 10, 1984

A self-lubricating fill tube comprises an extended conduit having a coating of hydrophillic polymer extending over at least a portion of an outer surface of the conduit. A method for forming the self-lubricating fill tube by cleaning and irradiating the fill tube with gamma radiation in a dosage of about 0.5 Mrads. The fill tube is immersed in a ethylenically unsaturated monomer solution containing oxidizable metallic ions which initiate polymerization of the monomer onto the exposed surface of the fill tube. The fill tube is removed from the monomer solution leaving a hydrophilic polymer coating on the surface of the fill tube. The polymer coated fill tubes are rinsed with deionized water.

U.S. Pat. No. 4,509,947

Inventor: Gary A. Lattin

Issued: Apr. 9, 1985

A drug delivery catheter and storage bladder adapted for use in an implantable drug delivery system. The catheter and bladder are provided with piezoelectric layers adapted to be responsively coupled to a source of ultrasonic electrical signals. When so coupled, vibration of the piezoelectric layer dislodges any accumulation of crystallized drugs within the catheter and bladder.

U.S. Pat. No. 4,696,667

Inventor: Helmut Masch

Issued: Sep. 29, 1987

An intravascular catheter includes a flexible guide wire mounted for relative rotational and reciprocal movement within a reciprocal and flexible first tube or sheath. A rotary and flexible second tube is mounted for relative reciprocal movement on the first tube and has a rotary inner cutting head is closely fitted within an outer cutting head that is slidably mounted on the first tube. In carrying out the method of this invention, a blockage in a blood vessel, such as a coronary artery, is located and the outer cutting head engages the blockage to cut the blockage into fragments in response to rotation of the inner cutting head. The fragments are flushed-out from the inner cutting head and are drained through an evacuated annular passage defined between the first and second tubes.

U.S. Pat. No. 4,698,058

Inventor: Albert R. Greenfeld et al.

Issued: Oct. 6, 1987

Vibration is conveyed to the proximal orifices of an indwelling catheter to disintegrate accumulated clogging deposits, large suspended particles and contaminating bacteria, viruses, fungi, etc. orifices may be recessed, hooded or enclosed, and in some cases the catheter tip should be of absorptive material, to deter propagation of the vibration to the parts of the patient's body outside the catheter. Vibration may be conveyed to the orifices by (1) a solid fiber embedded in the catheter walls or positioned in an auxiliary lumen of the catheter; or (2) by a liquid in an auxiliary lumen - which may be formed as an annular space surrounding the main lumen. Preferably the apparatus measures the amount of vibration absorbed by the deposits or bacteria, etc., as a function of frequency, and automatically concentrates the vibration at frequencies where absorption is particularly high, to maximize the disintegration of deposits, particles, bacteria or other bioactive objects. Ultrasonic shear waves are thought more effective than compressional waves, but both may be used.

U.S. Pat. No. 5,030,213

Inventor: William E. Rumberger

Issued: Jul. 9, 1991

A catheter router assembly is disclosed for clearing salt blockages in a previously inserted catheter. A length of flexible, stainless steel cable is provided and a silver solder tip is applied at the proximal end of the cable. The silver solder tip is then machined to form a suitable cutting edge for cutting or drilling through the body salts which clog the catheter. A pin vise is secured along the length of the flexible power cable to facilitate insertion of the cable into the catheter and to provide hand rotative power to the cutting tip sufficient to cut through the blocking salts and to clear the catheter for further use. The pin vise may be readily moved along the length of the power cable as necessary to define sufficient free, unsupported forward portions of the cable to reach and clear the blockage throughout the entire length of the catheter.

U.S. Pat. No. 5,492,530

Inventor: Robert E. Fischell et al.

Issued: Feb. 20, 1996

The present invention is a method for using an improved guiding catheter that eliminates the need for an introducer sheath or a separate Tuohy-Borst "Y" adaptor, thus reducing the time and expense for performing artery opening procedures. Furthermore, the guiding catheter with straightening dilator as described herein allows the hole in the wall of the femoral artery in the arm to be approximately 2 French sizes smaller in diameter as compared to the hole that would be created if an introducer sheath is also used. The advantages of the present invention are accomplished by utilizing a guiding catheter with a dilator that has a stiffened and/or curved distal section that can be used to straighten the distal section of the guiding catheter as it is advanced through the arterial system. The guiding catheter plus dilator can then be used in a manner similar to an introducer sheath to percutaneously enter the artery by being advanced over a previously placed guide wire. Once the distal ends of the dilator and the guiding catheter are placed near the ostium of the coronary artery, the dilator and guide wire are withdrawn which allows the guiding catheter to assume its normal bent shape (e.g., a Judkin's bend) near its distal end. The cardiologist can then, by well known techniques, place the guiding catheter's distal end in the ostium of a coronary artery. Any of several well known procedures can then be performed including angiography, balloon angioplasty, atherectomy or stent placement.

U.S. Pat. No. 5,653,696

Inventor: Samuel Shiber

Issued: Aug. 5, 1997

A process and apparatus for removing obstruction material from a stent which is located in a vessel in a body. The process generally involves threading a flexible casing into the material, and optionally, passing a tubular blade over the material to separate the material from the stent, and then withdrawing the flexible casing and the material out of the stent.

SUMMARY OF THE PRESENT INVENTION

The present invention relates generally to catheters and, more specifically, to a device able to be readily connected to an end of a catheter for breaking up and removing obstructions within a lumen of the catheter and a method for breaking up an obstruction within a catheter.

A primary object of the present invention is to provide a catheter cleaning device and method that will overcome the shortcomings of prior art devices.

Another object of the present invention is to provide a catheter cleaning device and method able to provide a non surgical means for breaking up an obstruction within and thus de-clogging a catheter.

A further object of the present invention is to provide a catheter cleaning device and method able to be easily used by health care professionals to declog a catheter.

Yet another object of the present invention is to provide a catheter cleaning device including an adapter for affixing the device to the proximal end of the catheter.

Still yet another object of the present invention is to provide a catheter cleaning device including a guide wire which can be selectively extended into the distal end of the catheter.

An even further object of the present invention is to provide a catheter cleaning device including a guide member able to ride along the length of guide slots between the proximal and distal ends of the housing for moving the guide wire into and out of the catheter.

Yet another object of the present invention is to provide a catheter cleaning device wherein the wire is selectively extended to the distal end of the catheter by the guide member and the device includes transversal guide slots in the housing for rotating the guide member and guide wire when fully extended into the catheter.

Another object of the present invention is to provide a catheter cleaning device wherein the adapter for attaching the device to a catheter is able to guide the guide wire into the catheter as it is extended into the lumen of the catheter.

A still further object of the present invention is to provide a catheter cleaning device wherein the distal end of the guide wire bows slightly upon contact with the catheter obstruction, wherein, when the guide member reaches the terminus of the guide slot it is rotated within the transverse guide slots, permitting the guide wire to break up the obstruction as opposed to piercing the obstruction.

A yet further object of the present invention is to provide a catheter cleaning device able to be manufactured to varying lengths whereby the length of the guide wire is substantially equal to the length of the catheter preventing the guide wire from extending beyond the distal end of the catheter.

Another object of the present invention is to provide a catheter cleaning device that is simple and easy to use.

A still further object of the present invention is to provide a catheter cleaning device that is economical in cost to manufacture.

Additional objects of the present invention will appear as the description proceeds.

A catheter cleaning device for clearing a catheter of obstructions is disclosed by the present invention. The catheter cleaning device includes an elongate hollow housing including first and second slots extending along opposing sides thereof and first and second lateral slots extending perpendicular to a respective one of the first and second slots, a guide member encircling the housing and including a bar extending across a diameter thereof and through both the first and second slots, a guide wire extending from the bar and an adapter for connecting the device to the catheter. The adapter includes a recess extending therethrough for the guide wire to pass out of the housing and into the catheter. The first and second lateral slots allow for rotation of the guide member and thus turning of the guide wire. Turning of the guide wire causes the guide wire to scrape against the obstruction thereby breaking the obstruction into smaller pieces and clearing the catheter. The guide wire has a length substantially equal to a length of the catheter and an end of said guide wire is able to bow upon contacting the obstruction.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

Figure 6:
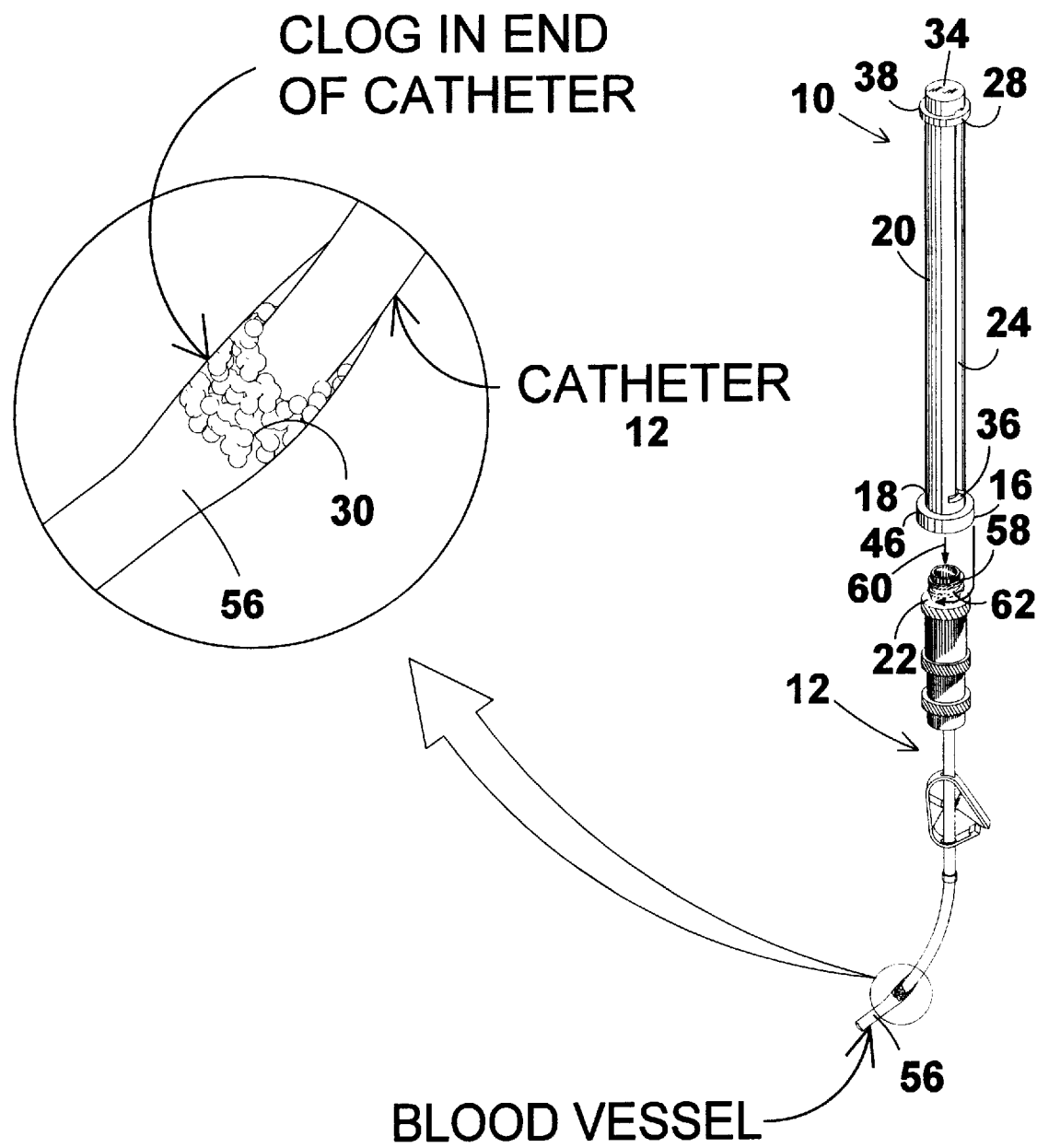
Figure 7:
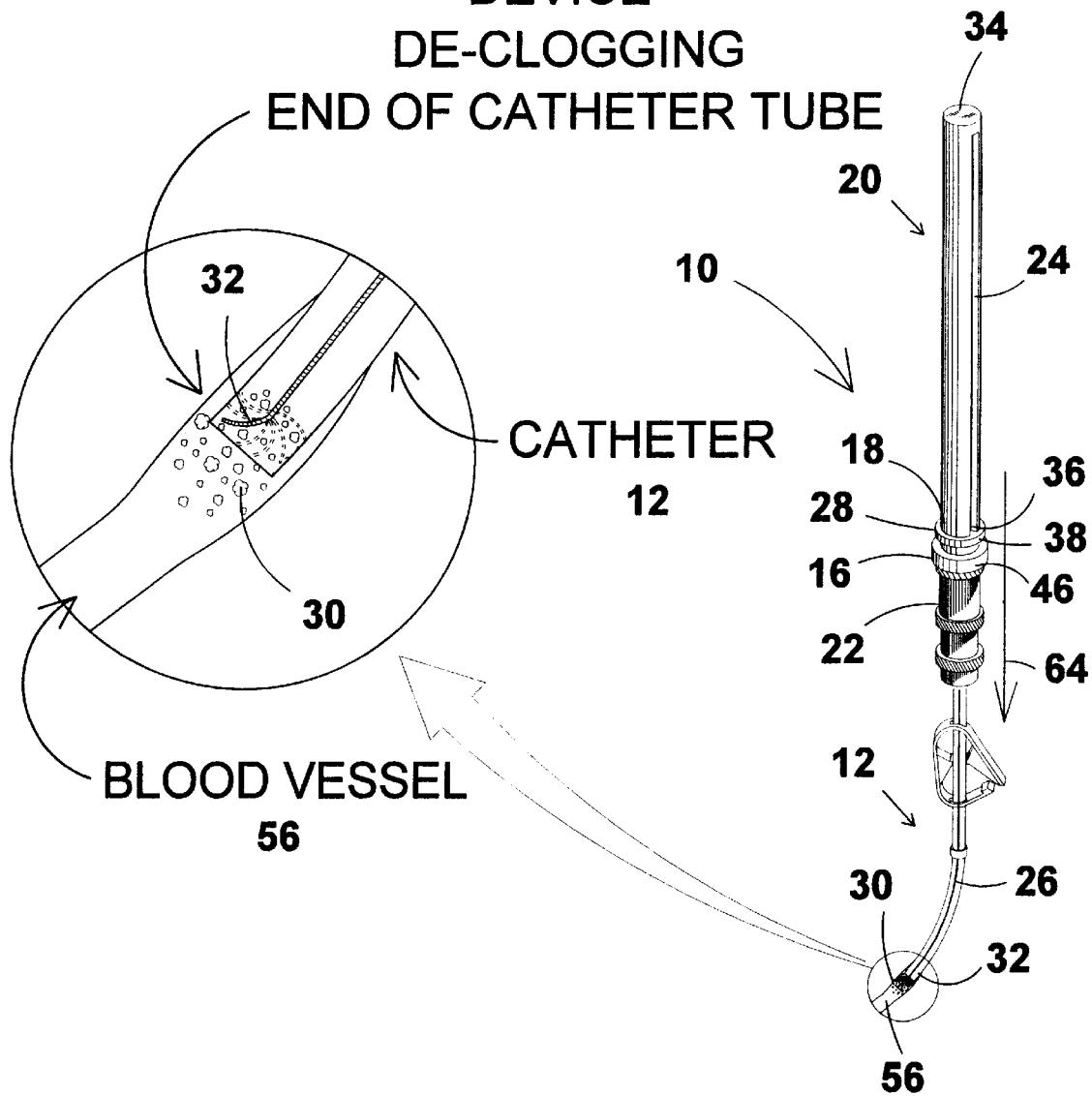

FIG. 6 is a perspective view of the catheter cleaning device of the present invention immediately prior to being affixed to a catheter having an obstruction therein and an enlarged view of the obstruction within the blood vessel; and FIG. 7 is a perspective view of the catheter cleaning device of the present invention affixed to the catheter having an obstruction therein and an enlarged view of the obstruction within the blood vessel and the guide wire clearing the obstruction.

DESCRIPTION OF THE REFERENCED NUMERALS

Turning now descriptively to the drawings, in which similar reference characters denote elements throughout the several views, the Figures illustrate the catheter cleaning device method of the present invention. With regard to the reference numerals used, the following numbering is used throughout the various drawing figures.

10 catheter cleaning device of the present invention
12 catheter
14 patient
16 adapter
18 first end of the catheter cleaning device
20 housing
22 proximal end of catheter
24 slot along length of housing
26 guide wire
28 guide member
30 blockage within catheter
32 end of guide wire which is extended into the catheter
34 second end of housing
36 transverse slot
38 outer peripheral surface of guide member
40 bar extending across diameter of outer peripheral surface
42 central section of bar
44 funnel shaped recess in adapter
46 skirt extending from around funnel shaped recess
48 thread spiraling around inner side of skirt
50 inner side of skirt
arrow indicating direction of guide member and guide wire into extended position
54 arrow indicating length of guide wire
56 blood vessel
58 thread around distal end of catheter
60 arrow indicating direction of movement of device for connection to catheter
62 arrow indicating direction of rotation of device to engage with catheter
64 arrow indicating direction of movement of guide wire into extended position

DETAILED DESCRIPTION OF THE PREFERRED EMBODIMENT

Turning now descriptively to the drawings, in which similar reference characters denote similar elements throughout the several views, FIGS. 1 through 7 illustrate the catheter cleaning device of the present invention indicated generally by the numeral 10.

Figure 1:
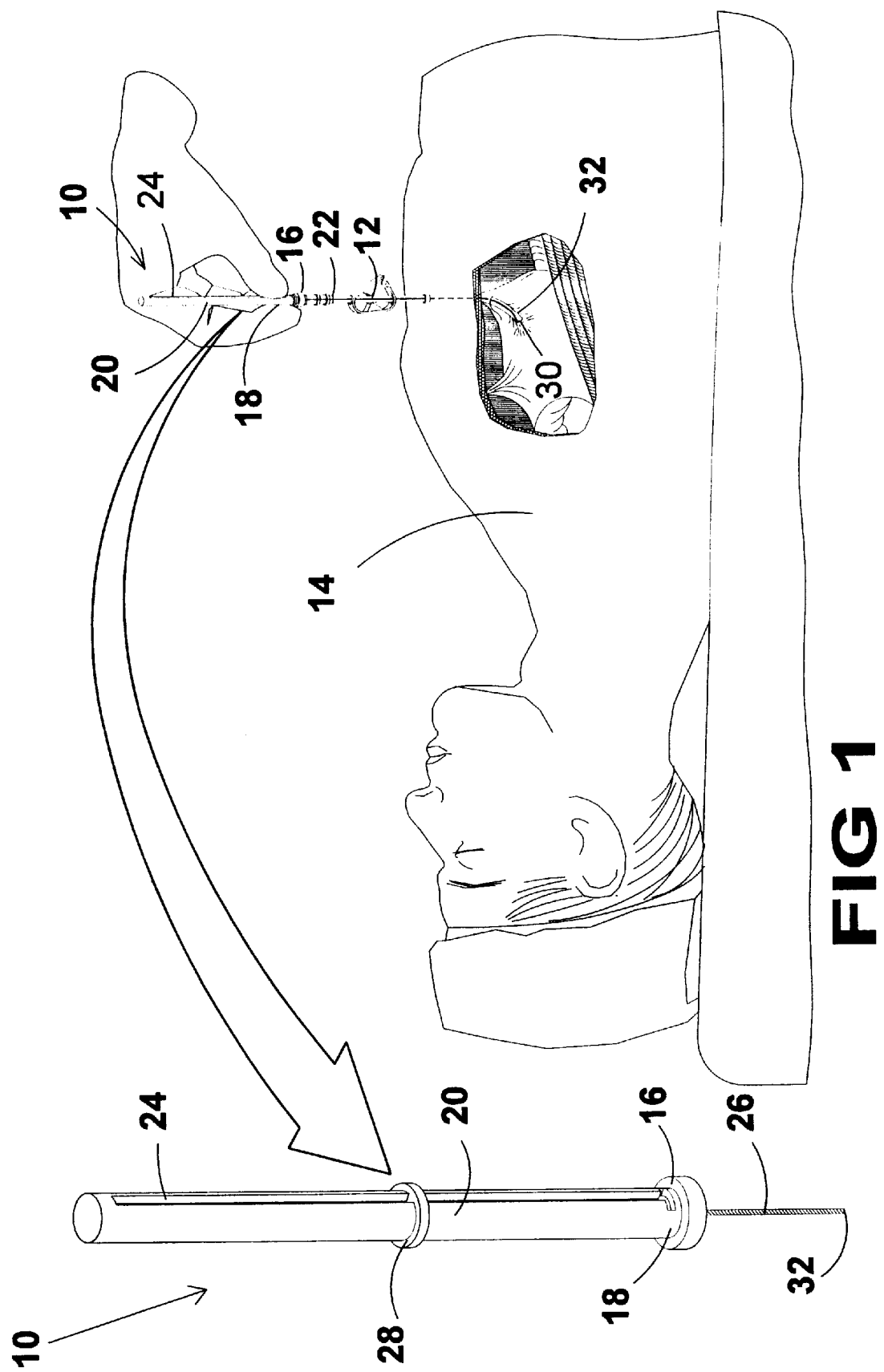
FIG. 1 is a perspective view of the catheter cleaning device of the present invention connected to a catheter implanted in a patient having a blockage and an enlarged view of the catheter cleaning device of the present invention.

The catheter cleaning device 10 is shown in FIG. 1 releasably connected to a catheter 12 implanted in a patient 14. An enlarged view of the catheter cleaning device 10 is shown on the right side of FIG. 1. As can be seen from this figure, the catheter cleaning device 10 includes an adapter 16 extending from a first end 18 of a housing 20 for connecting the catheter cleaning device 10 to a proximal end 22 of the catheter 12. Extending along a length of the housing 20 are a pair of opposing slots 24, only one of the pair of slots 24 is visible from the angle shown in this figure. A guide member 28 is slidably connected to the housing 20 and rides along the length of the slots 24. A guide wire 26 is connected to a guide member 28 and is caused to be extended from and retracted into the housing 20 as the guide member 28 slides along the length of the pair of opposing slots 24. The guide member 28 is shown positioned at the first end 18 of the housing 20 with the guide wire 26 fully extended into the catheter 12 and engaging a blockage or obstruction 30 within the catheter 12. The guide wire 26 is formed of a material which allows an end 32 thereof to bow upon coming into contact with the blockage 30.

Figure 2:
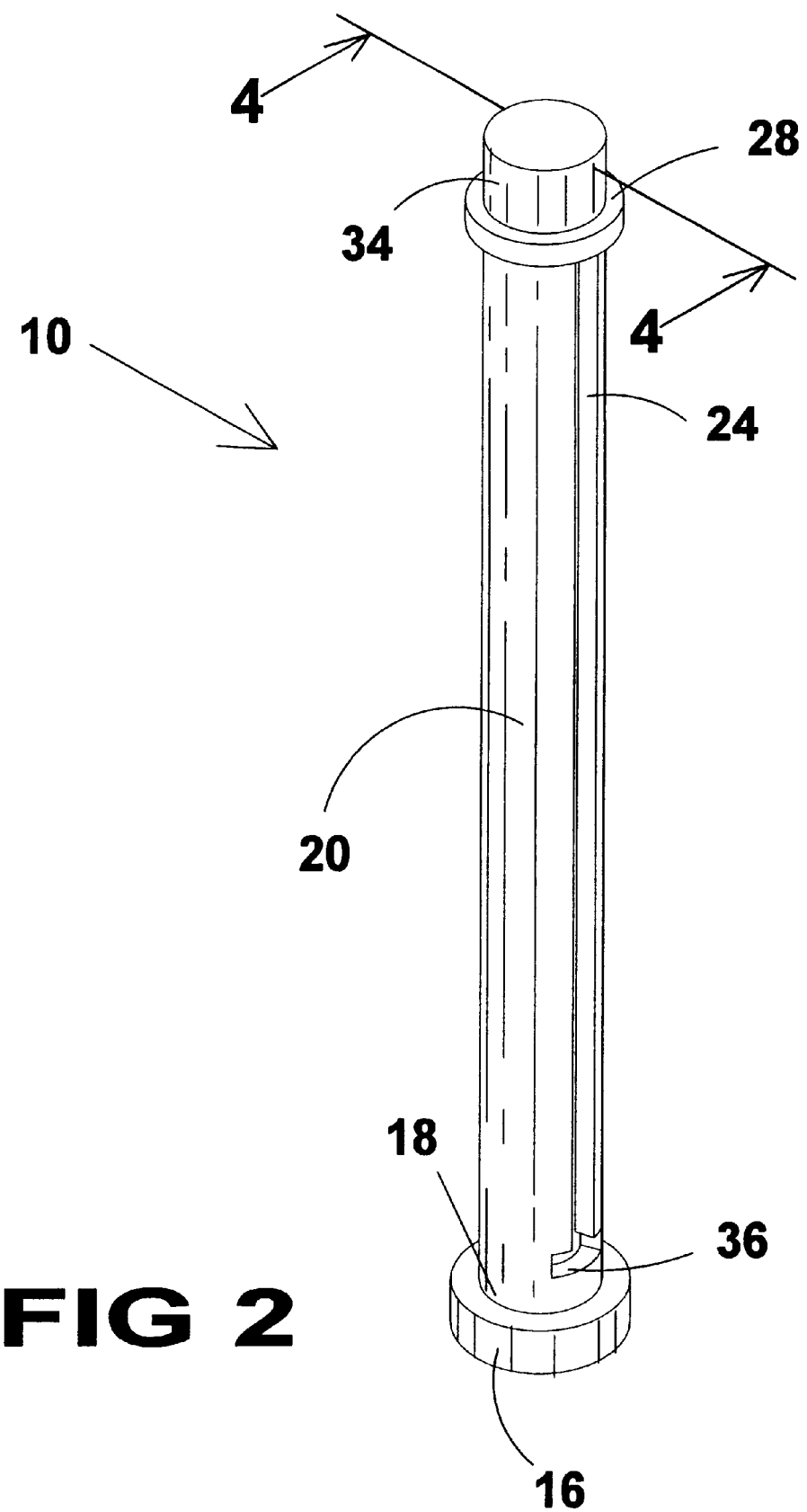
FIG. 2 is a perspective view of the catheter cleaning device of the present invention.

A perspective view of the catheter cleaning device 10 is shown in FIG. 2. This figure shows the guide member 28 positioned at a second end 34 of the housing 20 with the guide wire 26 in a fully retracted position within the housing 20. At the base of the vertical slot 24 is a transverse slot 36. The transverse slot 36 allows the guide member 28 to turn therein along with the guide wire 26 when placed in a fully extended position. When the guide wire 26 is in a fully extended position and contacts an obstruction 30 within the catheter 12 the guide member 28 may be turned causing the guide wire 26 to scrape against the obstruction 30 thereby breaking up the obstruction 30 and allowing for easy removal of the obstruction 30 from within the catheter 12.

Figure 3:
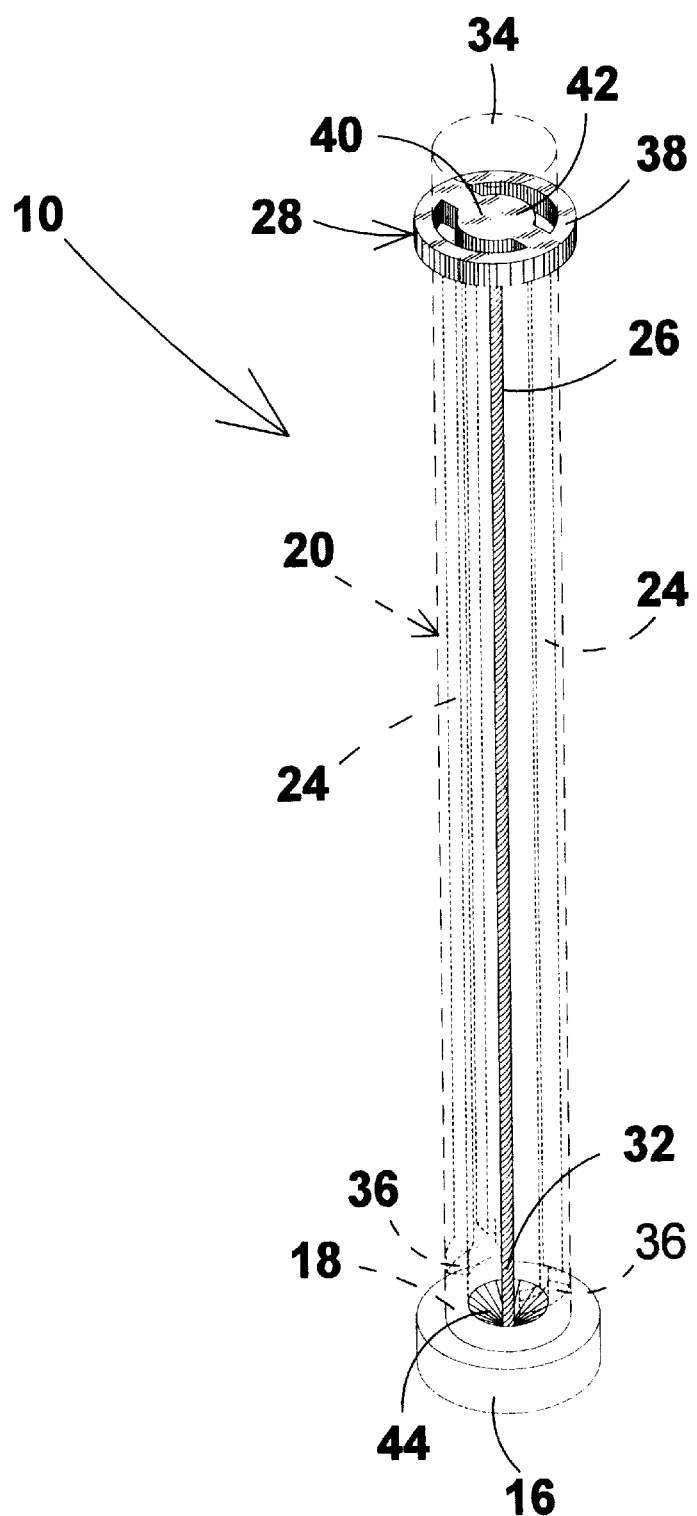
FIG. 3 is a perspective view of the catheter cleaning device of the present invention with the housing shown in dashed lines.

A view of the catheter cleaning device 10 with the housing 20 shown in dashed lines is illustrated in FIG. 3. This view allows the components of the catheter cleaning device 10 positioned within the housing 20 to be viewed. As can be seen from this view the guide member 28 is positioned at the second end 34 of the housing 20 and the guide wire 26 is connected to extend therefrom and along the length of the housing 20. The guide member 28 is preferably circular in shape and includes an outer peripheral surface 38 encircling the housing 20. A bar 40 extends through the opposing slots 24 and across the diameter of the outer peripheral surface 38. The guide wire 26 is connected to extend from a central section 42 of the bar 40. The guide wire 26 is substantially equal to the length of the catheter cleaning device 10 such that when the guide member 28 is in a fully retracted position at the second end 34 of the housing 20, the guide wire 26 will be completely contained within the housing 20. The adapter 16 is positioned at the first end 18 of the housing 20 and includes a funnel shaped recess 44 extending therethrough. The funnel shaped recess 44 acts as a guide for guiding the guide wire 26 out of the catheter cleaning device 10 and into the catheter 12 connected thereto.

Figure 4:
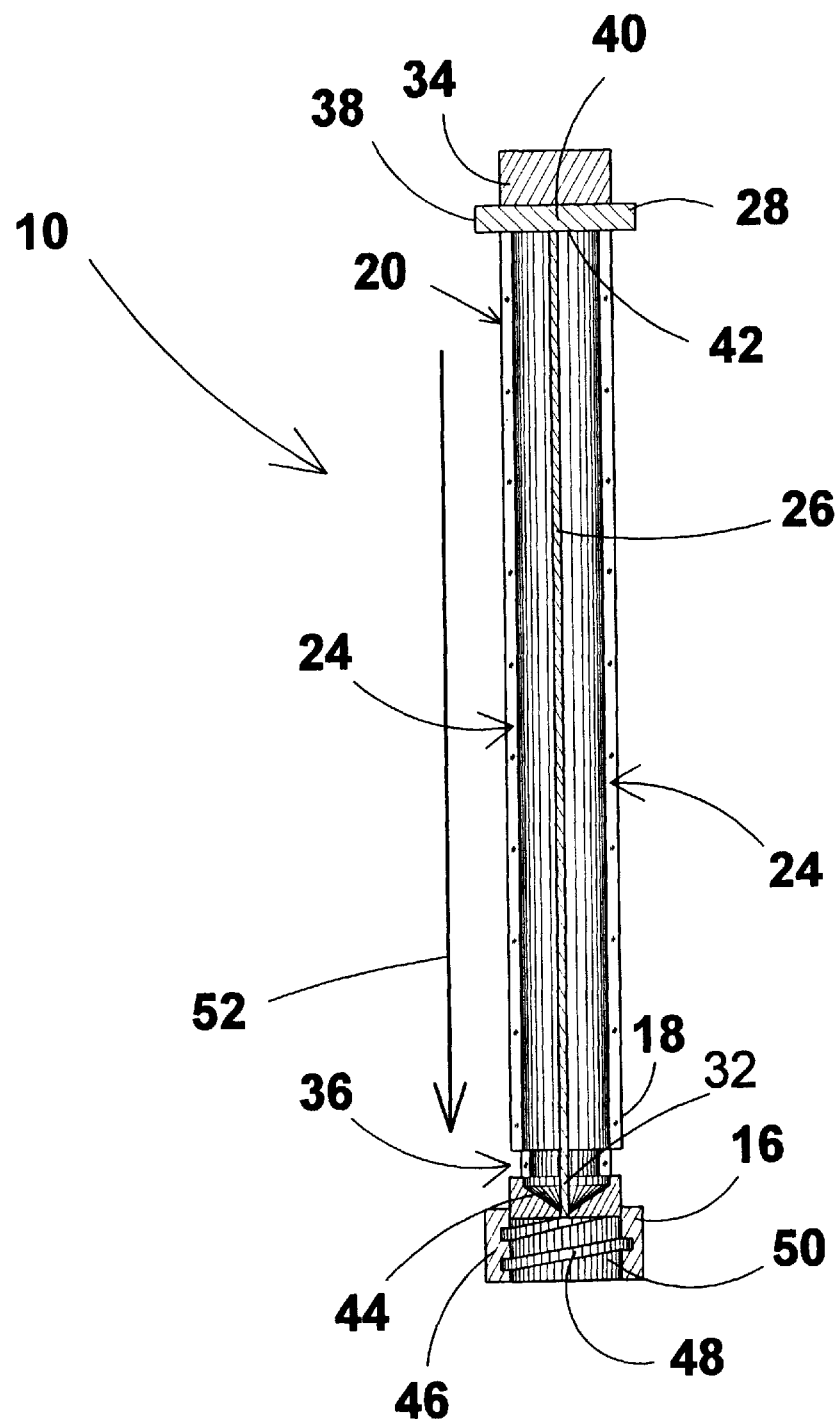
FIG. 4 is a cross sectional view of the catheter cleaning device of the present invention.
Figure 5:
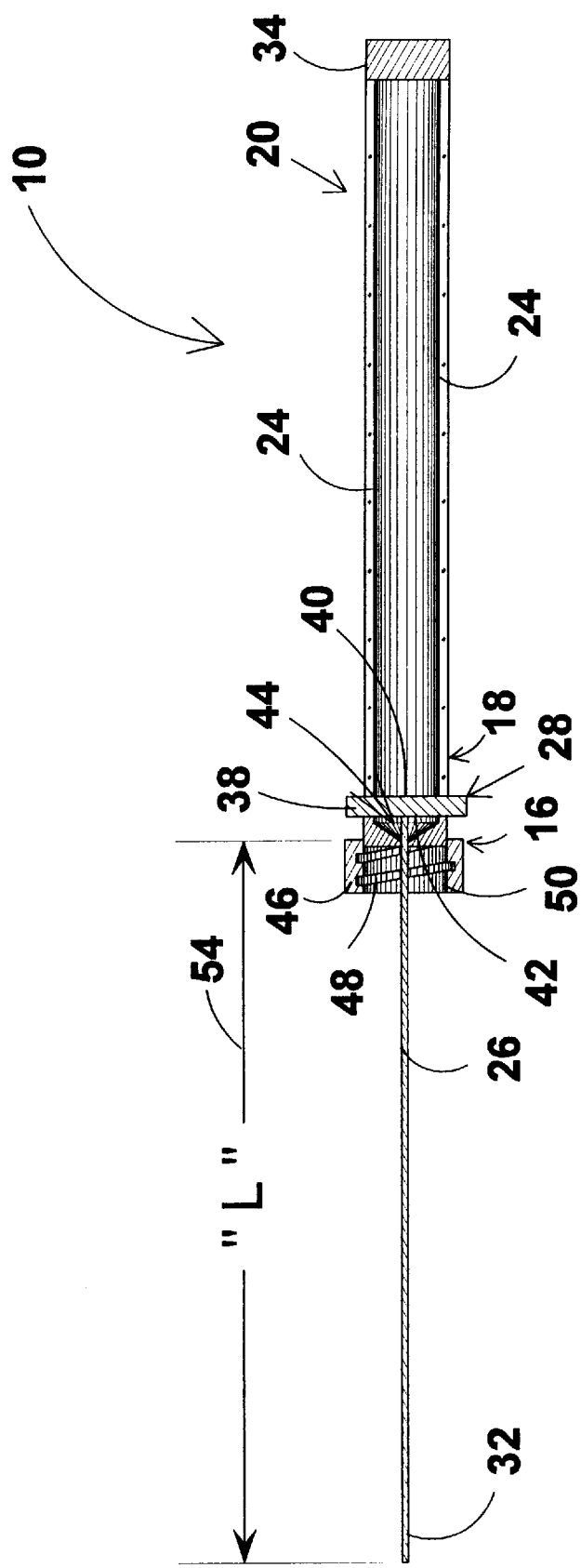
FIG. 5 is a cross sectional view of the catheter cleaning device of the present invention showing the extendible retractable member in an extended position whereby the guide wire is fully extended from the housing.

A cross-sectional view of the catheter cleaning device 10 with the guide member 28 and guide wire 26 in the retracted position is shown in FIG. 4. The guide member 28 and guide wire 26 are shown in the extended position in FIG. 5. This figure shows the pair of slots 24 positioned on opposing sides of the housing 20. The transverse slots 36 are shown connected to a respective one of the opposing slots 24 at the first end 18 of the housing 20. The funnel shaped recess 44 is positioned below the transverse slots 36 at an exit point for the guide wire 26 from the housing 20. Extending from a side of the funnel shaped recess 44 opposite the transverse slots 36 is a skirt 46 including a thread 48 spiraling around an inner side 50 thereof. The thread 48 is provided to engage a thread spiraling around an outer side of the distal end 22 of the catheter 12 to which the catheter cleaning device 10 will be connected. An arrow labeled with the numeral 52 is provided in FIG. 4 to show the direction of movement for the guide member 28 and guide wire 26 into the extended position. The guide wire 26 is shown in the fully extended position with its length indicated by the arrow |L| labeled with the numeral 54 in FIG. 5.

The operation of the catheter cleaning device 10 will now be described with reference to the figures and specifically FIGS. 6 and 7. In operation, the catheter cleaning device 10 is used for cleaning obstructions from within catheters 12 connected to a blood vessel 56 and implanted within a patient's body 14. An end 22 of the catheter 12 protrudes from the body 14 of the patient and includes a connector at the end 22 for connection of the catheter cleaning device 10. The end 22 includes a thread 58 spiraling therearound. When preparing the catheter cleaning device 10 for use in removing an obstruction 30 from within the catheter 12, the adapter 16 of the catheter cleaning device 10 is moved in the direction indicated by the arrow labeled with the numeral 60 towards the end 22 of the catheter 12. Once the adapter 16 is positioned against the end 22, the catheter cleaning device 10 is turned clockwise as indicated by the arrow labeled with the numeral 62. As the catheter cleaning device 10 is turned in this direction, the thread 48 on the inner side 50 of the adapter 16 is caused to engage the thread 58 spiraling around the end 22 of the catheter 12. Once the threads 48 and 58 are fully engaged, the catheter cleaning device 10 is ready for use.

The guide member 28 is now moved along the length of the pair of opposing slots 24 in the direction of the arrow labeled with the numeral 64 until the guide member 28 reaches the bottom of the slots 24 and can not move any further. At this point the guide member 28 is aligned with the transverse slots 36 and the guide wire 26 is fully extended into the catheter 12. The length of the guide wire 26 is substantially equal to the length of the catheter 12 such that when in the fully extended position, the guide wire will extend to the opposite end of the catheter 12. The catheter cleaning device 10 is thus able to clear any obstruction along the entire length of the catheter 12.

When in this position, the guide wire 26 is able to contact the obstruction 30. When the guide wire 26 contacts the obstruction 30, the end 32 of the guide wire 26 contacting the obstruction 30 is caused to bow slightly. At this point, the person clearing the obstruction grasps the guide member 28 and turns the guide member 28 back and forth along the length of the transverse slots 36. As the guide member 28 is turned, the guide wire 26 is also caused to turn back and forth, scraping the obstruction 30 as it turns. As the guide wire scrapes the obstruction 30, the obstruction 30 is caused to break away from the sides of the catheter 12 and also break up into smaller pieces as indicate din the enlarged view shown in FIG. 7. As the obstruction 30 breaks up, it is caused to exit the catheter 12 and is carried through the blood vessel 56 thus clearing the catheter 12 for use.

Once the obstruction 30 is cleared, the guide member 28 is moved along the length of the pair of slots 24 causing the guide wire 26 to be retracted from within the catheter 12. The guide member 28 is moved until it reaches the second end 34 of the slots 24. At this point the guide wire 26 is fully contained within the housing 20. The catheter cleaning device 10 is then removed from its engagement with the catheter by turning the adapter 16 in a counterclockwise direction causing the threads 48 and 58 to become disengaged.

From the above description it can be seen that the catheter cleaning device of the present invention is able to overcome the shortcomings of prior art devices by providing a catheter cleaning device which is able to provide a non surgical means for breaking up an obstruction within and thus de-clogging a catheter and may be easily used by health care professionals to declog a catheter. The catheter cleaning device includes a guide wire which can be selectively extended into the distal end of the catheter, a guide member able to ride along the length of guide slots between the proximal and distal ends of the housing for moving the guide wire into and out of the catheter and an adapter for affixing the device to the proximal end of the catheter and guiding the guide wire into the catheter as it is extended into the lumen of the catheter. The guide wire of the catheter cleaning device is selectively extended to the distal end of the catheter by the guide member and the device further includes transversal guide slots in the housing for rotating the guide member and guide wire when fully extended into the catheter. The catheter cleaning device is also able to be manufactured to varying lengths whereby the length of the guide wire is substantially equal to the length of the catheter preventing the guide wire from extending beyond the distal end of the catheter. Furthermore, the catheter cleaning device of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A catheter cleaning device for clearing a catheter of obstructions, said catheter cleaning device comprising:
   a) an elongate hollow housing including first and second slots extending along opposing sides of said housing;
   b) a guide member encircling said housing and including a bar extending across a diameter thereof and through both said first and second slots;
   c) a guide wire extending from said bar; and
   d) means for connecting said device to the catheter, said connecting means including a recess extending therethrough and wherein said guide member is movable between a first retracted position wherein said guide wire is retained within said housing and a second extended position wherein said guide wire is extended through said connecting means, into said catheter and contacting any obstruction within the catheter for clearing the obstruction from blocking the catheter.

2. The catheter cleaning device as recited in claim 1, wherein said housing further comprises first and second lateral slots extending perpendicular to a respective one of said first and second slots at an end of said housing adjacent said connecting means, wherein said first and second lateral slots allow for rotation of said guide member.

3. The catheter cleaning device as recited in claim 1, wherein said guide member has a length substantially equal to a length of said catheter.

4. The catheter cleaning device as recited in claim 2, wherein said guide member has a length substantially equal to a length of said catheter.

5. The catheter cleaning device as recited in claim 3, the wherein an end of said guide wire is able to bow upon contacting the obstruction.

6. The catheter cleaning device as recited in claim 4, wherein an end of said guide wire is able to bow upon contacting the obstruction so that said guide wire scrapes against the obstruction when said guide member is rotated within said first and second lateral slots.

7. The catheter cleaning device as recited in claim 1, wherein said recess extending through said connecting means is funnel shaped for guiding said guide wire therethrough and into the catheter.

8. The catheter cleaning device as recited in claim 7, wherein said connecting means includes a skirt extending from around said funnel shaped recess and a thread spiraling around an inner side of said skirt for engaging a thread on an end of the catheter.

9. The catheter cleaning device as recited in claim 1, wherein said guide wire is contained within said housing when said guide member is in said retracted position.

10. The catheter cleaning device as recited in claim 6, wherein scraping of said guide wire against the obstruction causes the obstruction to break up into small pieces and be carried away in a vessel to which the catheter is connected.

* * * * *